United States Patent [19]

Modes et al.

[11] 4,311,152
[45] Jan. 19, 1982

[54] MEDICAL ELECTRODE AND SYSTEM FOR MINIMIZING MOTION ARTIFACTS

[75] Inventors: Vernon E. Modes, Kent; Hak W. Tam, Kirkland; Wayne E. Quinton, Seattle; Alan G. Bailey, Everett; Robert A. Niskanen; Lou Vitez, both of Seattle; Gary A. DeBardi, Redmond, all of Wash.

[73] Assignee: Quinton Instrument Co., Seattle, Wash.

[21] Appl. No.: 3,109

[22] Filed: Jan. 15, 1979

[51] Int. Cl.$^3$ .............................................. A61B 5/04
[52] U.S. Cl. .................................................... 128/641
[58] Field of Search ............................. 128/639–641, 128/644, 783, 798, 802, 803

[56] References Cited

U.S. PATENT DOCUMENTS

| 2,782,786 | 2/1957 | Krasno | 128/639 |
| 2,887,112 | 5/1959 | Smith | 128/644 |
| 3,774,592 | 11/1973 | Lahr | 128/640 |
| 3,911,906 | 10/1975 | Reinhold, Jr. | 128/641 |
| 4,004,578 | 1/1977 | Palmius | 128/640 |
| 4,027,664 | 6/1977 | Heavner, Jr. et al. | 128/641 |
| 4,126,126 | 11/1978 | Bare et al. | 128/639 |
| 4,166,453 | 9/1979 | McClelland | 128/639 |

OTHER PUBLICATIONS

Tam et al., "Minimizing Electrode Motion Artifact . . . ", IEEE Trans. on Bio med. Eng., vol. 24, No. 2, 3/1977, pp. 134–139.

Burbank et al., "Reducing Skin Potential Motion Artifact . . . ", Med. & Biol. Eng. & Comput., 1978, 16, 31–38.

Primary Examiner—Lee S. Cohen
Attorney, Agent, or Firm—Seed, Berry, Vernon & Baynham

[57] ABSTRACT

A medical electrode and skin preparation device is adapted to be secured to the skin and is designed to prepare the skin by penetration of the epidermal layer of the skin in contact with the electrical conductor of the electrode after the electrode is secured in place on the skin. The electrode includes abrading member associated with electrical conductor capable of transmitting biopotential events for recording, with the electrical conductor retained by a collar and adhesive-coated pad securing the electrode to the skin of the patient. The abrading member in contact with the skin is movable relative to the skin of the patient and collar by an applicator gun to penetrate the epidermal layer of skin after the electrode is placed on the skin. Uniform skin preparation achieved by the electrode and applicator gun minimizes motion artifacts arising from skin potential variations.

20 Claims, 7 Drawing Figures

MEDICAL ELECTRODE AND SYSTEM FOR MINIMIZING MOTION ARTIFACTS

BACKGROUND OF THE INVENTION

1. Field of the Invention

This invention relates to an improved surface mounted medical electrode which performs skin preparation prior to recording biopotential events. The electrode, after application to the skin, is employed to penetrate the epidermal layer of the skin for minimizing motion artifacts. The invention is also directed to a system for skin preparation in conjunction with electrode application, the system including a surface mounted medical electrode and a timed applicator for delivery through the mounted electrode of a prescribed amount of skin preparation by the electrode.

2. Prior Art Relating to the Disclosure

Motion artifacts can be defined as motion induced fluctuation of skin potential which manifests itself as electrical interference which is often superimposed on the desired biopotential signal and minimizes its usefulness for diagnostic and clinical purposes. Motion artifacts have long been a problem in measurement of biopotentials, particularly in longterm electrocardiogram (ECG) monitoring of coronary care patients and in exercise (stress) ECG's. They are generally caused by movement of the patient relative to the electrode applied to the patient's skin, thereby disturbing the skin potential and creating extraneous read-outs on the monitor which either mask the desired biopotential signal or cause a shift in the base line.

It is known that light abrasion of the skin reduces the skin potential as well as minimizes the skin impedance and thereby reduces motion artifacts and improves trace quality. Tam, Hak W., et al, "Minimizing Electrode Motion Artifact by Skin Abrasion", IEEE Trans. on Biomed. Engr., BME-24, No. 2, pp. 134–137 (March 1977).

Although there are many disposable surface mounted electrodes described in the literature and commercially available for cardiac monitoring, reliable trace results from these electrodes is highly dependent on adequate skin preparation prior to application of the electrodes. Proper skin preparation is time consuming as a regular stress ECG requires 3 to 12, generally 10 electrodes. Skin preparation is carried out in various ways. The most common method of preparing the skin is to rub the patient's skin in the areas where the electrodes are to be applied with a gritty material contained in a carrier or to rub the patient's skin with a rough surfaced material to which an alcohol or other solvent is applied. After briskly rubbing the skin, the skin is dried and again rubbed with a dry cloth. If, after the electrodes are applied, a proper trace is not obtained from one or more of the electrodes, the malfunctioning electrodes must be identified, removed, the skin again cleaned and the electrodes reapplied to assure an adequate and accurate trace. Different skin preparation techniques are employed by different individuals. The effectiveness of the skin preparation depends on the technique used as well as the level of skill of the person preparing the skin. Predictably, skin preparation in this manner is highly variable.

Applicants are not aware of any surface mounted medical electrodes suitable for recording biopotential measurements in which the electrode is first applied and then the skin prepared. Such an approach markedly reduces the time consumed in the application of electrodes for recording biopotential events. Also, more reliable, accurate and uniform traces are obtained since the amount and type of skin preparation for each electrode is uniform.

SUMMARY OF THE INVENTION

It is a primary object of this invention to provide a surface mounted medical electrode which performs skin preparation after application and before recording of biopotential events. The electrode is provided with a mobile conductive means and means associated therewith for penetration of the epidermal layer of skin that can be driven after application of the electrode to the skin to perform skin preparation and thereby minimize motion artifacts arising from skin potential variations and skin impedance. The electrode may be either pre-gelled or not pre-gelled and disposable or reusable. The conductive means of the electrode holds the epidermal penetrating means which may be provided with an electrolyte. The conductive means is secured for movement relative to an adhesive coated sheet member used to adhere the electrode to the skin. When the electrode is pre-gelled and is stored, it may be provided with a removable protective cover for the adhesive coated sheet member and for the penetrating means provided with electrolyte gel.

It is a further object of this invention to provide a surface mounted medical electrode capable of (1) a more uniform and consistent skin preparation patient to patient and (2) recording biopotential events.

It is a further object of this invention to provide a surface mounted medical electrode provided with a movable abrading member for abrading the skin after application of the electrode to the patient.

It is a further object of this invention to provide a surface mounted electrode which eliminates technique variability in skin preparation, which minimizes motion artifacts and which reduces the time necessary for application of the electrodes to a patient.

It is still a further object to provide a system, including a surface mounted medical electrode and timed applicator for skin preparation, the timed applicator delivering a prescribed amount of skin preparation through the electrode.

It is a further object of this invention to provide a surface mounted electrode including a conductive element which has a specially designed raised stud for coupling to a powered applicator so that the applicator can drive the conductive element even though the applicator may engage the stud at an angle.

It is still a further object of this invention to provide a specially designed applicator for use with surface mounted electrodes of the type described for delivering a prescribed amount of skin preparation through the electrode after application of the electrode to the skin.

DESCRIPTION OF THE PREFERRED EMBODIMENTS

Figure 1:
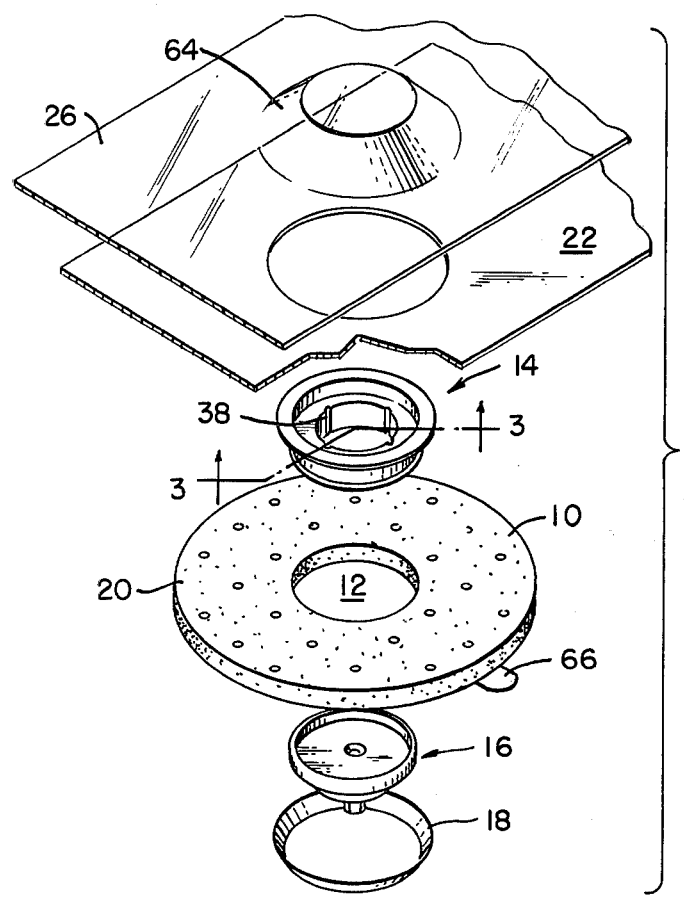
FIG. 1 is an exploded view of the surface mounted medical electrode of this invention, illustrating the components which make up the electrode except for the abrasive electrolyte-containing member.

FIG. 1 illustrates the surface mounted electrode of this invention which consists of a circular sheet member 10 having an annular cutout portion 12 in the center thereof in which a collar 14 is inserted, the collar holding an electrically conductive member 16 therein. A ring 18 may be employed to clamp around the upper portion of the collar 14. The sheet member 10 is coated on one side with a skin adhesive layer 20. The adhesive is protected during storage with a protective cover 22. An abrasive member 24 (see FIG. 2), provided with an electrolyte gel, is placed in contact with the conductive member 16 and is protected during storage with a protective cover 26.

The collar 14 has the configuration of an inverted hat having a flat base 28 and a vertical wall 30 normal and integral with the base terminating in a contoured flange 32. The base has an annular opening 34 in the center thereof with a diameter less than the diameter of the inner wall 30. Around the annular opening 34, is a vertical wall 36 having slots 38 cut therein about every 90 degrees. The function of the slots will be described in detail later. The walls 30 and 36 extend above the plane of the base 28 leaving a channel 40 therebetween. The holder is generally molded from a semi-flexible plastic material such as an acetate-based material, nylon, polyester, polyethylene or polypropylene. The wall 36 is made sufficiently thin so that it can be flexed under pressure. The diameter of the collar 14 is substantially greater than its height. The inner periphery of the wall 36 is provided with a ridge 42 whose function will be later described.

The electrically conductive member 16 is adapted to be held by the collar. The electrically conductive member may be manufactured from a synthetic resin impregnated with carbon, from a suitable electrically conductive metal or metal-containing material or other suitable electrically conductive material. The electrically conductive member 16 includes a lower portion 44 having a textured convex lower surface 45 and a thickness substantially equal to the depth of the cup formed by the flange 32, wall 30 and base 28 of the collar. Integral with the lower portion 44 is an upper portion 46 of reduced diameter relative to the lower portion, the upper portion 46 having a diameter equal to that of the annular opening 34 in the collar. The circumference of the upper portion has a slot 48 therein which is interrupted by detents 50 positioned normal to the slot 48. The vertical detects are spaced about every 72 degrees around the circumference of the upper portion. The conductive member 16 is snapped into place in the collar 14. The slot 48 of the conductive member receives the ridge 42 in the wall 36 of the collar to prevent the conductive member from moving vertically within the collar. The detents 50 engage in the slots 38 in the flexible wall 36 of the collar to prevent the conductive member from being rotated except by a predetermined torque/force. Application of sufficient torque to the conductive member 16 will cause the conductive member to rotate within the collar, the spacing of the detents 50 and slots 38 yielding a locking position about every 18 degrees.

Integral with the conductive member 16 is an upstanding stud 52 provided with a polygonal outer surface 54, preferably an eight-sided surface, so that the coupler of the applicator can be drivingly secured over the stud to rotate the conductive member.

Figure 2:
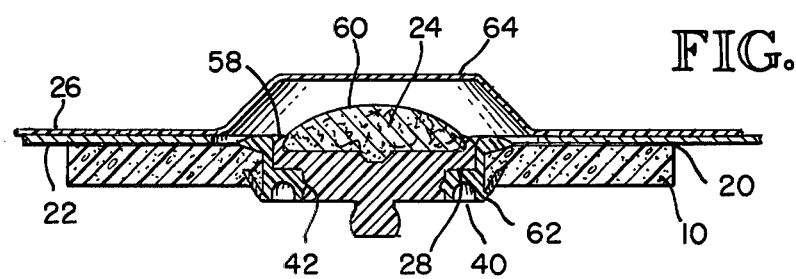
FIG. 2 is a vertical cross-section of the electrode of this invention.
Figure 3:
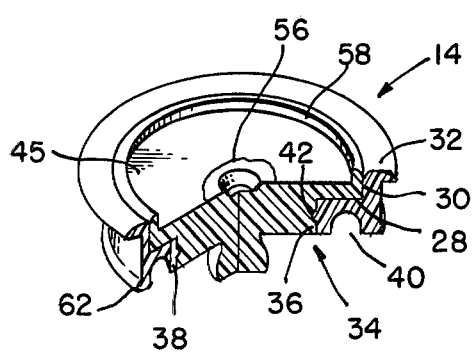
FIG. 3 is a perspective view of the conductive element and collar of the electrode illustrating the detent in the conductive element and notch arrangement of the collar for securing the conductive member against rotation when rotation is not desired.

The outer wall of the lower portion 44 of the conductive member 16 is provided with a thin walled extension 58 around the outer periphery thereof, as illustrated in FIG. 2.

The means for penetrating the epidermal layer of skin may be a separate abrasive member as illustrated, an abrasive member integral with the conductive member such as bristles forming the surface 45 of the conductive member, or other means capable of penetrating the epidermal layer of the skin when moved relative to the skin. The abrasive member 24 is a pad incorporating abrasive fibers and preferably having a convexly curved surface 60 and a diameter substantially the same as the diameter of the lower portion 44 is placed in contact with the surface 45 of the conductive member and the flange 58 folded against the edges of the pad to clamp the pad in place. The pad preferably has a thickness such that it extends above the plane of the flange 32 of the collar. The pad is loaded with electrolyte gel so that when the electrode is applied to the skin, the electrolyte gel makes good electrical contact between the skin and the conductive member 16.

The assembled collar 14, conductive member 16 and abrasive member 24 are placed in the annular opening 12 of the adhesive coated sheet member 10. The adhesive coating 20 contacts the upper surface of the flange 32 of the collar (see FIG. 2) to secure the collar in place relative to the sheet member. A snap ring 18 (which may be color coded) may be snapped over the top of the electrode around the wall 30 of the collar. The snap ring is held in place by a ridge 62 extending around the outer terminating edge of the wall 30 of the collar.

The adhesive which coats the sheet member is protected during storage and prior to use by a removable protective paper sheet 22 having a release coating on its face which engages the adhesive coating 20. A protective cover 24 may also be provided for the abrasive member when provided with electrolyte gel so that the electrode may be stored in a ready condition for immediate use. The cover may take any shape desired. The cover illustrated is made of a flat strip of non-conductive plastic sheet material having raised portions 64 which overlie the abrasive member of the electrode. The sheet of plastic material is adhered to the removable protective sheet 22 by a suitable adhesive. The protective cover may be made of any suitable plastic material such as polyethylene, polyvinyl butyrate, cellulose acetate, etc. After the electrodes are assembled with the protective covering, they may be stored for indefinite periods of time until needed. Preferably, the electrode is packaged in an air and water tight package to avoid dehydration of the electrode gel during storage. Such packaging is conventionally used.

Generally, the electrodes are placed on a strip of protective sheet material 22 in groups of three or more. When the electrodes are ready to be used, the electrode is peeled from the surface of the protective paper and placed on the skin in the location desired without prior preparation of the skin. The protective sheet, when peeled away, takes the protective cover for the abrasive member with it. If desired, the sheet member 10 may have a tab 66 extending beyond the outer periphery of the sheet member so that the person applying the electrodes can grasp the tab and remove the electrode from the protective sheet 22 without touching and compromising the adhesive coated on the underside of the pad.

The dimensions of the electrode, while not particularly critical, are sized for optimum reliability and accurate body placement. The diameter of the sheet member surrounding the holder is generally two to three times the diameter of the collar. Sufficient area should be provided for skin contact by the pressure-sensitive adhesive to adequately hold the electrode to the skin of the patient. The adhesive used on the sheet member may be any of the commercially available medical grade pressure-sensitive adhesives currently being used on disposable medical electrodes. The sheet member may be a microporous material such as Micropore tape sold by the 3M Company or a polyethylene or polyvinyl choride foamed plastic. The foamed sheet member may be perforated with multiple perforations as illustrated in FIG. 1 to allow adequate ventilation of the skin.

While the preferred embodiment of the electrode described above abrades the skin by rotation of the conductive member and abrasive member after the electrode is adhered to the skin, the invention is intended to include other means of providing motion of the means capable of penetrating the epidermal layer of skin relative to the patient's skin to prepare the skin. The invention is further intended to include other configurations of the abrasive member which, when caused to move with respect to the patient's skin, creates abrasion or puncture of the epidermis.

Figure 5:
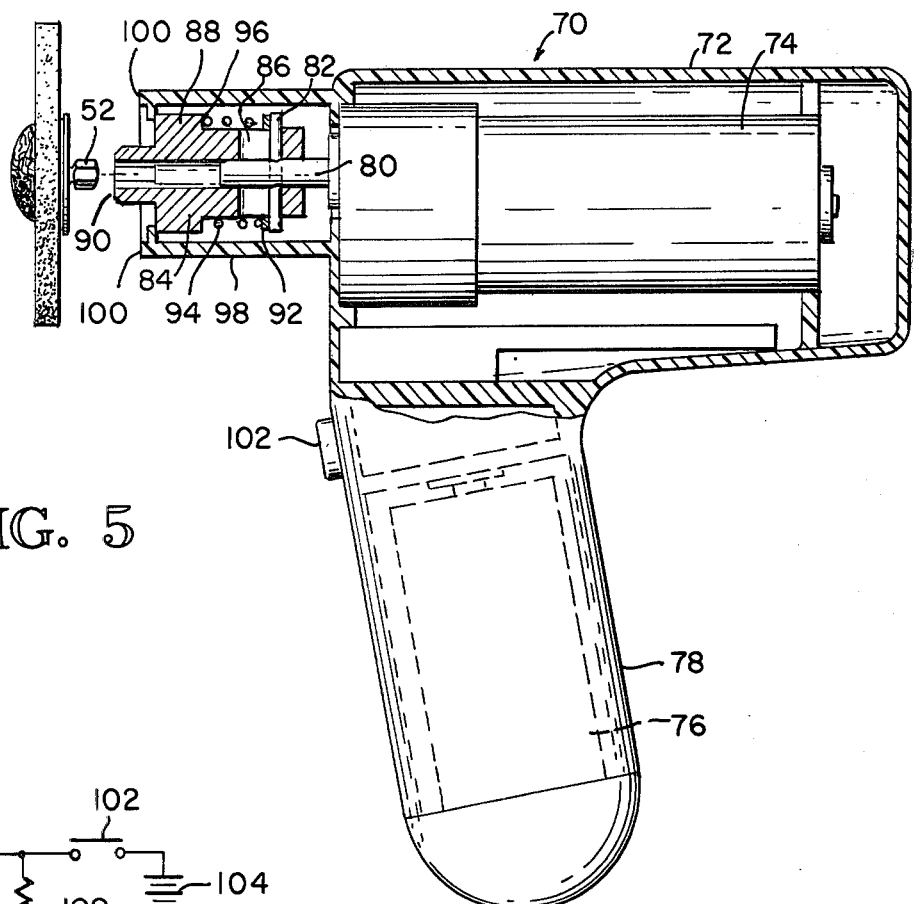
FIG. 5 is a schematic view of the applicator used to drive the movable conductive element and abrasive member of the electrode to perform skin preparation.
Figure 6:
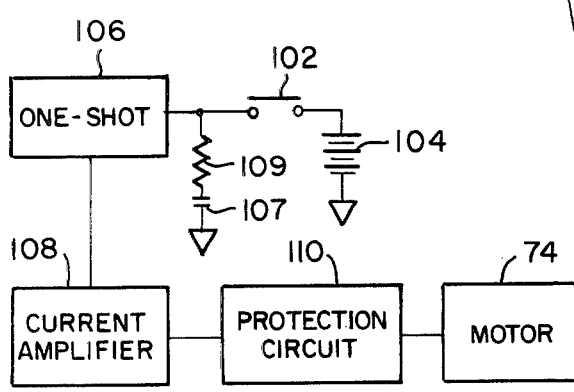
FIG. 6 is a block diagram of the timing control circuit of the applicator.
Figure 7:
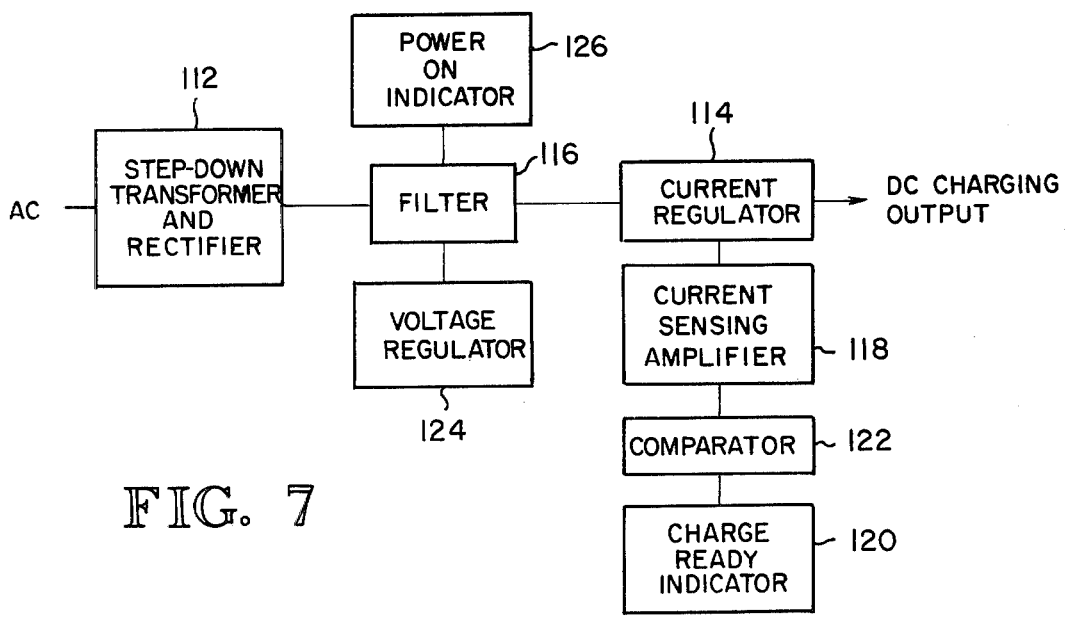
FIG. 7 is a block diagram of the charge status indicator circuit of the applicator.

FIGS. 5, 6 and 7 illustrate, respectively, the applicator 70 and electrical block diagrams of the timing/control circuit and charge status indicator circuit for the applicator used to prepare the skin of the patient after application of the electrode thereto. Referring to FIG. 5, the applicator includes a housing 72 within which is mounted an electric motor 74 driven by AC or DC current from a suitable current source. The motor illustrated is driven by a rechargeable battery 76 held in place in a quickly disconnectable case 78 which also serves as the handle of the applicator. The lower end of the case includes recessed electrical contacts (not shown) for battery recharging. The motor has a shaft 80 to which a coupler is attached.

FIG. 5 illustrates the coupler in more detail. The shaft 80 is provided with a laterally extending pin 82 as illustrated. A sleeve 84 having an elongated slot 86 therein slips over the shaft with the pin 82 riding in the slot 86. The head 88 of the coupler is integral with the sleeve and includes a polygonal member 90 which drivingly engages the stud member 52 of the electrode. A ring 92, slipped over the sleeve of the coupler, engages the pin 82. Spring 94 extends between shoulder 96 of the head 88 of the coupler and the ring 92 to bias the coupler in the forward position illustrated in FIG. 5. The spring is sized such that when the applicator engages the electrode, it will deliver a prescribed amount of pressure against the skin for adequate skin preparation. The coupler is housed within a housing 98 with the wrench end 90 of the coupler protruding to engage the stud of the electrode. Referring to FIG. 5, the wrench end 90 of the applicator engages the stud 52 of the electrode. Sufficient pressure is applied by the operator of the applicator to retract the coupler and allow the terminating edges 100 of the applicator to rest against the electrode. Once engaged, the applicator is timed to deliver a prescribed amount of skin preparation through the electrode. Generally, with the applicator rotating at 500 rpm the time is less than five seconds at an applied pressure of about 0.75 lbs. The motor of the applicator is energized by switch 102.

Figure 4:
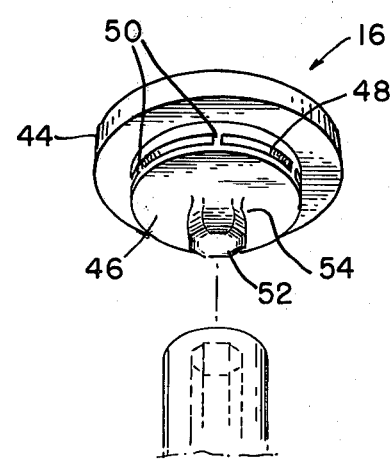
FIG. 4 is a perspective view of the projecting stud of the conductive member and the coupler of the applicator gun illustrating the manner in which the applicator is connected to the stud for rotation of the conductive member by the applicator.

FIG. 4 illustrates the manner in which the wrench end 90 of the applicator engages the stud 52 of the conductive member for rotation. The exterior surface of the stud has an octagonal configuration so that the wrench can drivingly engage the stud at an angle other than normal to the stud. This is important for the person applying the electrodes in that the angle of the applicator relative to the stud is not critical to proper driving engagement of the stud and the applicator. The octagonal stud functions in a similar manner to a universal joint allowing the coupler of the applicator to drivingly engage it over a range of angles varying from normal.

FIGS. 6 and 7 schematically illustrate the timing/control circuit for the applicator and the charge/status indicator circuit which indicates to the operator whether the applicator is adequately charged for use. Referring to FIG. 6, the switch 102 of the applicator is pressed to close the circuit from the battery 104 thereby triggering a one-shot 106. The one-shot 106 generates a pulse having a duration determined by capacitor 107 and resistor 109. The pulse is amplified by a current amplifier 108 and passes through a conventional protection circuit 110 to activate the motor 74 of the applicator. Thus, the motor 74 rotates for a predetermined duration each time the switch 102 is actuated.

FIG. 7 illustrates one method of charging the rechargeable batteries 76 of the applicator. The charger includes a status indicator circuit which indicates to the operator whether the batteries of the applicator are adequately charged for use. Current from a conventional 110 volt AC source is converted to direct current by a transformer and rectifier 112. The output from the transformer and rectifier 112 flows through a current regulator 114 by way of filter 116 to the batteries to be charged. A current-sensing amplifier 118 senses the current draw of the current regulator 114 and indicates by way of the charge ready indicator 120 and comparator 122 the status of the charge of the battery. The current delivered to the batteries is regulated by voltage regulator 124. A power-on indicator 126 is provided to tell the operator whether the charge unit is functioning.

When ready for use, the electrodes are peeled away from the protective paper and protective covering and placed on the skin of the patient where desired. The applicator is engaged with the stud of the respective electrodes and activated to rotate the conductive element and the abrasive member to abrade the skin in contact with the abrasive member. The convex surface of the abrasive member concentrates abrasion of the skin near its center. The pressure and time used as well as the abrasive characteristics of the abrasive member are such that the epidermis is not adequately removed to expose nerve endings or capillaries. Penetration of the epidermis may cause skin irritation, particularly if an electrolyte having a high concentration of a soluble salt is used. Preparation of the epidermis provided by the electrode and applicator enables use of an electrolyte gel having a salt concentration which is relatively isotonic to minimize gel irritation.

The sensor for the electrode may be any suitable metal/metal salt combination having low polarization characteristics such as silver/silver chloride. A coating 56 of the metal is provided on the planar surface 45 of the conductive member. When silver is used, it may be desirable to form a layer of silver chloride on the silver layer coated on conductive surface of the conductive member. The layer of silver chloride may be formed in various ways. One convenient method is to pass an electric current through the electrolyte soaked abrasive member and conductive member to electrolytically form a layer of silver chloride on the surface of the silver layer.

The combined use of the electrode and applicator enables a systematized and consistent approach to skin preparation and electrode application. The extensive preparation of the skin of a patient prior to application of surface mounted electrodes of the prior art is not necessary with the electrode of this invention. Skin preparation is uniformly performed after the electrode is applied.

We claim:

1. An integral medical electrode and skin preparation device for improving the quality of biopotential event detection by minimizing motion artifact arising from skin potential, comprising:
   an electrically conductive member to which electrical connection to an external electrically responsive recorder can be made;
   skin abrading means in contact with the electrically conductive member, the skin abrading means establishing electrical contact between the skin of the patient and the electrically conductive member on application of the electrode to the skin; and
   holding means for holding the electrically conductive member out of direct contact with the skin of a patient when the electrode is applied, for holding the skin abrading means against the skin of the patient and preventing movement of the electrically conductive member and skin abrading means relative to the skin of the patient except on application of a sufficient amount of force to the electrically conductive member after application of the electrode to the skin to cause the skin abrading means to move relative to the skin sufficiently to penetrate the epidermal layer thereof.

2. The electrode and skin preparation device of claim 1 wherein the electrically conductive member is provided with a stud for connection to the electrically responsive recorder.

3. The electrode and skin preparation device of claim 2 wherein applicator means having a coupler is connected to the stud of the electrically conductive member through the coupler for rotating the conductive member and skin abrading means after application of the electrode.

4. An integral medical electrode and skin preparation device which allows preparation of the skin of a patient to reduce motion artifacts after application of the electrode to the skin of the patient, comprising:
   an electrically conductive member having a surface facing the skin when the electrode is adhered to the skin,
   holding means holding the electrically conductive member for rotation relative thereto,
   a flexible sheet member secured to the holding means having an adhesive coated on a surface thereof to be adhered to the skin of the patient, and
   an abrasive member loaded with an electrolyte gel in contact with the surface of the electrically conductive member and with the skin of the patient when the electrode is secured to the skin of the patient, the conductive member and the abrasive member rotatable relative to the skin, holding means and the sheet member adhering the electrode to the skin to abrade the portion of the skin in contact with the abrasive member sufficiently to minimize motion artifact.

5. The electrode and skin preparation device of claim 4 wherein the abrasive member is a resilient pad loaded with electrolyte gel and incorporating abrasive fibers.

6. The electrode and skin preparation device of claim 4 wherein the conductive member is circular and provided with a stud opposite the surface thereof contacting the abrasive member for connection to an electrically responsive recorder and wherein the holding means is a collar including an annular opening provided with a flexible wall holding the conductive member therein but allowing the conductive member to be rotated relative to the collar on application of a predetermined amount of torque.

7. The electrode and skin preparation device of claim 4 wherein the surface of the abrasive member contacting the skin of the patient is convex to concentrate abrasion of the patient's skin near the center.

8. An integral disposable pre-gelled medical electrode and skin preparation device which allows preparation of the skin of a patient to reduce motion artifacts after application of the electrode to the skin, comprising:
   an electrically conductive member having a surface facing the skin of the patient when the electrode is placed on the skin and an opposing stud for connection to an external electrically responsive monitor,
   an electrically non-conductive collar holding the conductive member, the collar including an annular opening provided with a flexible wall, the annular opening receiving the electrically conductive member therein and holding it against rotation relative to the collar except on application of a predetermined amount of torque,
   a flexible sheet member having an adhesive coating on a surface thereof provided with an annular opening therein receiving and adhesively bonding the collar therein,
   an abrasive member loaded with an electrolyte gel in contact with the surface of the electrically conductive member and contacting the skin of the patient when the electrode is secured to the patient,
   a removable protective cover over the adhesive coating on the sheet member during storage of the electrode, and
   a removable cover over the abrasive member during storage of the electrode, the cover having a raised portion overlying the abrasive member.

9. The electrode and skin preparation device of claim 8 wherein the flexible wall of the collar includes vertical slots therein and wherein the portion of the electrically conductive member contacting the flexible wall includes vertical detents which lodge in the slots and prevent rotation of the electrically conductive member except on application of a predetermined amount of torque.

10. The electrode and skin preparation device of claim 9 wherein the flexible wall of the collar and portion of the electrically conductive member contacting the flexible wall include means securing the electrically conductive member in the collar.

11. The electrode and skin preparation device of claim 8 wherein the exterior surface of the stud has an octagonal configuration.

12. The electrode and skin preparation device of claim 8 wherein the flexible wall of the collar is notched at intervals around its circumference and wherein the outer periphery of the electrically conductive member includes detents which lodge in the notches of the collar so that the conductive member is held against movement except on application of a predetermined amount of torque.

13. A combination medical electrode and applicator gun which allows preparation of the skin of a patient to reduce motion artifact after application of the electrode to the skin of the patient, comprising:

an electrically conductive member having a surface facing the skin when the electrode is adhered to the skin and a stud opposite the surface;

holding means holding the electrically conductive member for rotation relative thereto;

a flexible sheet member secured to the holding means having an adhesive coated on a surface thereof to be adhered to the skin of a patient;

an abrasive member loaded with an electrolyte gel in contact with the surface of the electrically conductive member and with the skin of the patient when the electrode is secured to the skin of the patient, the conductive member and abrasive member rotatable relative to the skin, holding means and flexible sheet member adhering the electrode to the skin; and an applicator, including a coupler detachably connected to the stud of the conductive member, generating sufficient torque to rotate the conductive member and abrasive member relative to the skin of the patient, holding means and sheet member to abrade the portion of the skin in contact with the abrasive member sufficiently to minimize motion artifact.

14. The electrode and applicator gun of claim 13 wherein the applicator includes a rotatable shaft driven by a motor, the coupler mounted on one end of the shaft, and a rechargeable battery operatively connected to the motor for driving the motor.

15. The electrode and applicator gun of claim 4 including timing means operatively connected to the motor to control the time of rotation of the shaft and coupler.

16. The electrode and applicator gun of claim 13 wherein the flexible sheet member is a perforated elastic foam material which allows escape of perspiration of the patient after the electrode is adhered to the skin.

17. The electrode and applicator gun of claim 13 including a removable protection sheet covering the adhesive layer of the flexible sheet member during storage of the electrode and a removable protective cover over the abrasive member.

18. The electrode and applicator gun of claim 17 wherein a portion of the outer edge of the flexible sheet member is provided with a release tab which overlies the outer edge of the flexible sheet member so that the electrode may be removed from the protective sheet without touching the adhesive layer.

19. The electrode and applicator gun of claim 13 wherein the coupler of the applicator is biased in a forward direction.

20. The electrode and applicator gun of claim 13 wherein the exterior surface of the stud has an octagonal configuration and wherein the coupler drivingly engages the stud at angles varying from normal.

* * * * *